United States Patent [19]

Widlund et al.

[11] Patent Number: 5,295,987
[45] Date of Patent: Mar. 22, 1994

[54] ABSORBENT DISPOSABLE ARTICLE WHICH IS DIVIDED INTO PORTIONS EXTENDING IN THE LONGITUDINAL DIRECTION OF THE ARTICLE

[75] Inventors: Leif U. R. Widlund, Mölnlycke; Roy Hansson, Mölndal, both of Sweden

[73] Assignee: Molnlycke AB, Gothenburg, Sweden

[21] Appl. No.: 859,460

[22] PCT Filed: Dec. 14, 1990

[86] PCT No.: PCT/SE90/00835
§ 371 Date: May 29, 1992
§ 102(e) Date: May 29, 1992

[87] PCT Pub. No.: WO91/09579
PCT Pub. Date: Jul. 11, 1991

[30] Foreign Application Priority Data

Dec. 21, 1989 [SE] Sweden ............................ 8904318

[51] Int. Cl.⁵ .......................................... A61F 13/15
[52] U.S. Cl. ............................ 604/385.2; 604/385.1; 604/358
[58] Field of Search .................. 604/385.1, 385.2, 368, 604/378, 370

[56] References Cited

U.S. PATENT DOCUMENTS

| | | | |
|---|---|---|---|
| 4,323,070 | 4/1982 | Ternström et al. | 604/385.2 |
| 4,897,084 | 1/1990 | Ternström et al. | 604/385.2 |
| 4,973,325 | 11/1990 | Sherrod et al. | 604/385.1 |
| 5,037,417 | 8/1991 | Ternström et al. | 604/385.2 |
| 5,099,532 | 3/1992 | Thomas et al. | 604/385.1 |
| 5,129,893 | 7/1992 | Thorén | 604/385.2 |
| 5,151,091 | 9/1992 | Glaug et al. | 604/385.1 |

FOREIGN PATENT DOCUMENTS

| | | |
|---|---|---|
| 3205931 | 9/1983 | Fed. Rep. of Germany . |
| 0450454 | 6/1987 | Sweden . |
| 2074011 | 10/1981 | United Kingdom . |

Primary Examiner—Randall L. Green
Assistant Examiner—Rob Clarke
Attorney, Agent, or Firm—Young & Thompson

[57] ABSTRACT

An absorbent, disposable article, such as a diaper, an incontinence guard or a sanitary napkin, which includes an outer liquid-impermeable casing layer which is intended to lie distal from the wearer in use, an inner, liquid-permeable casing layer which is intended to face toward the wearer's body in use and an absorbent pad enclosed between the two casing layers. The crotch part of the pad that is placed in the crotch region of the wearer in use is divided into mutually separate parts, which extend in the longitudinal direction of the article. These separate parts are mutually separated transversely, intermediate originally flat and pleatable areas of the two casing layers which are mutually joined and bridge the space between the separate parts. There is transverse elastication within the region of the separate parts of the absorbent pad, the elastication bringing the edges of adjacent separate parts into abutment with one another while gathering together the intermediate originally flat areas of the mutually joined casing layers.

5 Claims, 2 Drawing Sheets

ABSORBENT DISPOSABLE ARTICLE WHICH IS DIVIDED INTO PORTIONS EXTENDING IN THE LONGITUDINAL DIRECTION OF THE ARTICLE

The present invention relates to disposable absorbent articles, such as diapers, incontinence guards or sanitary napkins, which comprise an outer liquid-impermeable casing layer which is intended to face away from the wearer's body in use, an inner liquid-permeable casing layer which is intended to face towards wearer's body in use, and an absorbent pad enclosed between the two casing layers Such articles are mass produced, normally by being manufactured in a flat state, i.e. substantially flat absorbent bodies or pads are placed on a moving web of material and a further web of material is placed on the first mentioned web and fastened thereto in regions which lie outside the absorbent pads, whereafter a finished article is cut from the web. Although such articles can be manufactured readily at requisite production rates, the shape of the finished article does not conform well to the shape of the user's body, since the manufactured article is essentially flat. Consequently, when putting on an article that has been manufactured in this way, it is necessary to deform the article in order to cause it to conform to the shape of the wearer's body. This incurs the serious risk of forming folds or pleats in the article or of forming gaps between the article and the wearer's body when putting on the article. These folds and gaps greatly increase the risk of leakage.

In order to improve the shape conformity of such articles and also to reduce the risk of lateral leakage, such articles will often be provided with leg and waist elastication, and it is also known to utilize patterns of pre-stretched elastic threads or bands in a manner to impart a basin-like configuration to the article or to parts thereof.

The object of the present invention is to provide an absorbent disposable article, such as a diaper, an incontinence guard or a sanitary napkin, which will fulfill the high requirements placed on shape conformity and which is suitable for manufacture in a flat state and therewith at low production costs.

This object is achieved in accordance with the invention in that an absorbent disposable article of the kind mentioned in the introduction is characterized in that the absorbent pad is divided into mutually separate parts which extend in the longitudinal direction of the article, at least within the crotch part thereof, i.e. that region of the article which, in use, is intended to be placed in the vicinity of the user's crotch; in that said pad parts are mutually separated transversely in said crotch region by intermediate, mutually attached parts of the two casing layers; and in that transverse elastication is provided within the region of the separate parts of said absorbent pad such as to cause the edges of mutually adjacent, separate parts to move into abutment with one another while gathering together intermediate parts of the mutually fastened casing layers.

Because those regions of the mutually joined casing layer parts which separate the individual parts of the absorbent body are gathered together by the transverse elastication of the article in the last stage of the manufacturing process, i.e. the cutting stage, the overall cross dimensions of the article in this region will decrease. This means that the cross dimensions of those regions of the article which lie outside the extension of the longitudinally extending separate parts are also forced to decrease, which can only be realized by the article assuming a curved form in said regions. The invention thus results in a three-dimensional article.

According to one advantageous embodiment of the invention, the cross dimensions of the regions of mutually joined casing layers between adjacent separate parts of the absorbent pad in the extended state of said regions are greatest in the centre of the crotch part of the article, so as to be successively smaller in the longitudinal direction of said article, on both sides of the centre part of the crotch part, at least in the end parts of said regions. As a result, when said regions are gathered together in the aforesaid manner, the separate parts will also lift from the manufacturing plane of the article, in the regions of successively decreasing transverse dimensions of intermediate casing layers, since otherwise the mutually diverging or converging edges of adjacent separate parts could otherwise not come into abutment with one another. The desired three-dimensional configuration of the crotch part of the article can be readily achieved in this way, by suitable configuration of the edges of mutually adjacent separate parts of the absorbent pad and by dividing the absorbent pad in said crotch part into an appropriate number of parts.

When the absorbent pad consists essentially of cellulose fluff, as is normally the case, this division of the absorbent pad into several mutually separate parts within the crotch region of the article, each said part being enclosed between casing layers, results in improved mechanical strength against mechanical loads within the crotch part of the absorbent pad, as compared with an absorbent pad which is formed integrally in this region and has the same volume throughout. In the case of a pad produced in this way, there is less risk of the bonds between the fibres in the fluff breaking or rupturing in a manner such as to cause interruptions in all longitudinally extending capillary channels in the fluff and therewith prevent the dispersion of liquid in said longitudinal direction. Because of the small volume of each of the mutually separate parts of the absorbent pad, said parts being effectively held together by the casing layers, the risk of external loads causing the formation of or agglomerations in the absorbent pad is also reduced, i.e. the risk of individual fibres being moved in relation to adjacent fibres within the absorbent pad as a result of load, and therewith permanently hooking together.

A preferred embodiment of the invention will now be described in more detail with reference to the accompanying drawings, in which.

Figure 1:
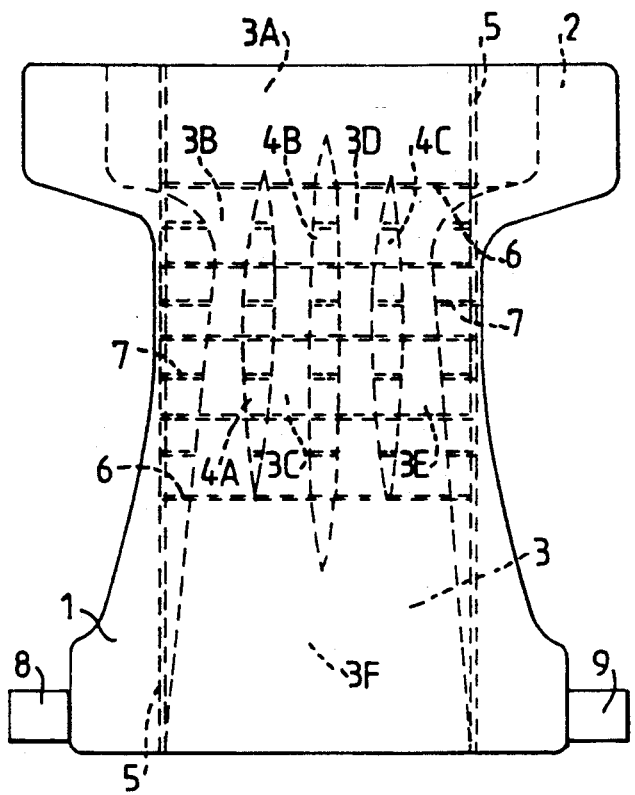
FIG. 1 is a schematic top view of an inventive diaper before the elastication has contracted.

The diaper illustrated in FIG. 1 includes an absorbent pad 3 which is enclosed between an outer liquid-impermeable casing layer 2 and an inner liquid-permeable casing layer 1, which in the top view of FIG. 1 faces towards the viewer and which is intended to lie closest to the child's body in use. The casing layers 1, 2 are joined together at parts which lie outside the pad 3.

The absorbent pad 3 is divided into several, mutually separate and longitudinally extending parts 3B-3E within the crotch part of the diaper, i.e. that part of the diaper which is intended to be placed in the region of the crotch of the wearer in use, and at the beginning of its front part 3A. The mutually separate parts 3B-3E are separated from one another in the transverse direction by mutually connected intermediate parts 4A-4C of the casing layers 1, 2.

The diaper also includes longitudinally extending elastic threads or bands 5, which extend beyond the absorbent pad on both sides of its rear part 3F and crotch parts 3B, 3E, and also externally of the central part of the front pad part 3A.

Transverse elastic threads or bands 6, 7 extend between the longitudinally extending elastic threads or bands 5 within the region of the mutually separate parts 3B-3E of the pad 3. The threads 6 which in the FIG. 1 embodiment extend over the parts 3B-3E, alternate with the threads 7 in the longitudinal direction of the diaper, the transverse threads 7 extending beneath the mutually separate parts 3B-3E in the case of the FIG. 1 embodiment.

The diaper is shown in FIG. 1 in its outwardly stretched or extended state, i.e. the state in which such a diaper is found during manufacture before the elastic threads 5-7 are allowed to contract.

Figure 2:
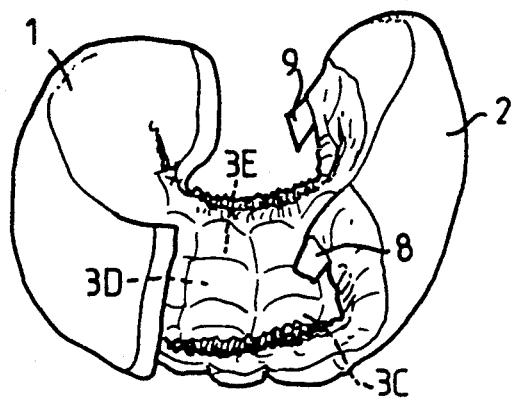
FIG. 2 is a perspective view of the diaper shown in FIG. 1 subsequent to contraction of the elastication.

FIG. 2 illustrates the diaper of FIG. 1 subsequent to contraction of the elastic threads 5-7, i.e. subsequent to having cut a finished article from the web. As will be seen from FIG. 2, this contraction of the elastic threads results in a significant change in the shape of the diaper, i.e. from its flat state shown in FIG. 1. The threads 6, 7 strive to move the edges of adjacent separate parts 3B-3E of the pad 3 into abutment with one another or into abutment with an intermediate, pleated part of the intermediate, mutually joined casing layer parts 4A-4C. As will be seen from FIG. 1, mutually adjacent edges of the separate parts 3B-3E of the pad 3 diverge from and converge towards each other, at least at the ends of the longitudinally extending separate parts 3B-3E. In order for these edges to come into abutment with one another, it is necessary for said parts to lift from the manufacturing plane of the diaper. Consequently, the crotch part can be given a desired three-dimensional shape, by appropriate configuration of the mutually separate parts and by using a suitable number of separate parts.

It will also be seen that contraction of the elastic threads 6, 7 and pleating or gathering of the casing layer parts 4A-4C will result in a reduction in the total cross-section dimensions of the diaper within the region of said mutually separate parts 3B-3E.

This reduction in the transverse dimensions of the diaper also means that the transverse dimensions of the diaper in the region of the parts 3A, 3F adjacent said mutually separate parts 3B-3E must also decrease. This is effected through curving of said parts, as illustrated in FIG. 2. This curving of said diaper parts is accentuated by the longitudinally extending elastic threads 5, which pull the side edges of the front and rear parts of the diaper towards one another.

In this connection, it is pointed out that the longitudinally extending elastic threads 5 will also be curved by contraction of the elastic threads 6, 7, therewith well to the shape of the wearer's body.

The diaper illustrated in FIG. 2 has thus taken a three-dimensional shape which, in principle, conforms with the shape of a diaper when worn. Consequently, the diaper is not subjected to any further appreciable deformation when it is put-on. As a result of dividing the absorbent pad into several mutually separate parts within the crotch region of said pad and because of the anatomically true shape of the diaper, there is obtained a diaper which has good shape stability in both a wet and a dry state. The regions 4A-4C also form narrow, longitudinally extending channels which promote the spreading of liquid discharges, by transporting liquid to deeper parts of the absorbent pad. These channels also counteract lateral dispersion of liquid on the surface of the liquid-permeable casing layer 1.

It will be understood that the diaper illustrated in FIGS. 1 and 2 can be modified in several ways. For instance, modifications can be made with regard to the number and the shape of the mutually separate parts of the absorbent pad, and the number of longitudinally and transversely extending elastic threads or bands. In one variant, the elastic threads 7 can extend above the parts 3B-3E of the absorbent pad, in the same manner as the threads 6. It may also be beneficial to provide the diaper with appropriately configured waist elastic.

Although the use of elastic threads is preferred, it will be understood that threads which shrink when treated in a subsequent stage is also conceivable. It is also conceivable to use elastic shrink film or the like.

Figure 3:
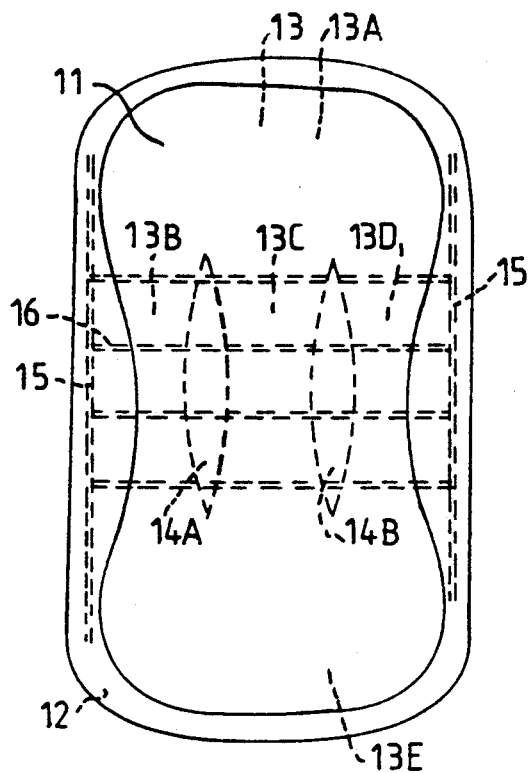
FIG. 3 is a schematic top view of an inventive sanitary napkin before the elastication has contracted.
Figure 4:
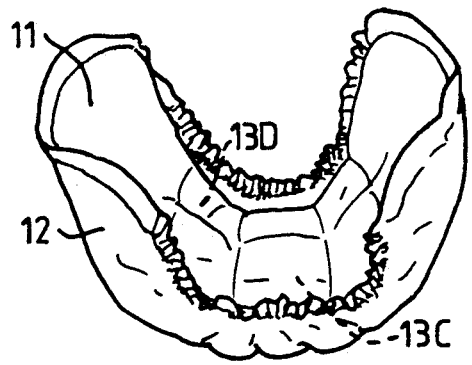
FIG. 4 is a perspective view of the sanitary napkin shown in FIG. 3 subsequent to contraction of the elastication.

FIGS. 3 and 4 illustrate a sanitary napkin configured in accordance with the present invention. The illustrated napkin includes an absorbent pad 13 which is enclosed between an inner, liquid-permeable casing layer 11 and an outer, liquid-impermeable casing layer 12, said pad being divided into three mutually separate parts 13B-13D within the crotch region of the napkin. The napkin also includes longitudinally extending and transversely extending elastic threads 15 and 16 respectively, which are disposed in the same manner as the threads 5 and 6 in the diaper shown in FIGS. 1 and 2. The threads 15 differ functionally from the threads 5, in that the threads 15 do not form leg elastication but have simply a napkin shaping function. An incontinence guard for women suffering mild incontinence can be advantageously formed in the same manner as the illustrated sanitary napkin.

The front and rear parts of the illustrated article embodiment are formed in one single piece It will be understood, however, that these parts, and then preferably the rear part, can be formed with a continuous, perforated absorbent pad provided that none of the perforations lies opposite one of the mutually separate parts in the crotch region of the article.

In summary, the invention provides an anatomically well-shaped absorbent disposable article of the kind defined in the introduction whose three-dimensional shape can be obtained despite producing the diaper in accordance with conventional, flat-manufacturing techniques.

We claim:

1. An absorbent, disposable article, such as a diaper, an incontinence guard or a sanitary napkin, which includes an outer liquid-impermeable casing layer which is intended to lie distal from the wearer in use, an inner, liquid-permeable casing layer which is intended to face toward the wearer's body in use and an absorbent pad enclosed between said two casing layers, wherein at least the crotch part of the pad that is placed in the crotch region of the wearer is divided into mutually separate parts, which extend in the longitudinal direction of the article, said separate parts being mutually separated transversely when the article is in an essentially flat state, intermediate originally flat and pleatable areas of the two casing layers being mutually joined and bridging the space between said separate parts, and transverse elastication means within the region of said separate parts of the absorbent pad, said elastication means bringing the edges of adjacent separate parts into abutment with one another while gathering together said intermediate originally flat areas of the mutually joined casing layers.

2. An article according to claim 1, wherein the quantity of gathered, mutually joined casing layer material between said longitudinally extending separate parts of the absorbent pad is greatest at the center of said crotch part and decreases progressively on both sides of the center of said crotch part longitudinally of the article.

3. An article according to claim 1, wherein said article includes also longitudinally extending elastic threads or bands, said elastic threads or bands being disposed between the casing layers externally or the outermost of the mutually separate parts of said pad.

4. An article according to claim 1, wherein each of the front and rear parts of the absorbent pad, in the longitudinally endmost parts of said absorbent pad, is configured as a single continuous part and wherein each of the ends of the mutually separate parts of the absorbent pad terminates in a said continuous part.

5. An article according to claim 1, wherein said separate parts of the pad are narrowest at the center of said crotch part and increase progressively in width on both sides of the center of said crotch part longitudinally of the article.

* * * * *